(12) United States Patent
Nelson et al.

(10) Patent No.: US 7,658,851 B2
(45) Date of Patent: Feb. 9, 2010

(54) METHOD OF GROWING BACTERIA FOR USE IN WASTEWATER TREATMENT

(75) Inventors: Douglas J. Nelson, Watertown, WI (US); Robert Rawson, Sebastopol, CA (US)

(73) Assignee: Pseudonym Corporation, Oswego, NY (US)

( * ) Notice: Subject to any disclaimer, the term of this patent is extended or adjusted under 35 U.S.C. 154(b) by 58 days.

(21) Appl. No.: 10/977,989

(22) Filed: Oct. 29, 2004

(65) Prior Publication Data

US 2009/0321350 A1    Dec. 31, 2009

Related U.S. Application Data

(60) Provisional application No. 60/516,067, filed on Oct. 31, 2003.

(51) Int. Cl.
*C02F 3/00* (2006.01)

(52) U.S. Cl. .................. 210/615; 210/616; 210/617; 210/618; 210/620

(58) Field of Classification Search ......... 210/615–618, 210/620
See application file for complete search history.

(56) References Cited

U.S. PATENT DOCUMENTS 6,982,032 B2 *    1/2006    Shaffer et al. ............... 210/101

* cited by examiner

*Primary Examiner*—Chester T Barry
(74) *Attorney, Agent, or Firm*—George R. McGuire; Bond Schoeneck & King, PLLC

(57) ABSTRACT

A device and method for growing aerobic and facultatively anaerobic bacteria such as *Pseudomonas Fluorescens, Bacillus subtilis, Bacillus licheniformis, Starkeya novella* and various autotrophic sulfur metabolizing bacteria, along with methods for releasing these bacteria into suspended growth or fixed film wastewater treatment zones such as soil or media, for the purposes of bioremediation and the removal of nitrogen, sulfur, and carbon wastes.

26 Claims, 1 Drawing Sheet

METHOD OF GROWING BACTERIA FOR USE IN WASTEWATER TREATMENT

CROSS-REFERENCE TO RELATED APPLICATION

Figure 1:
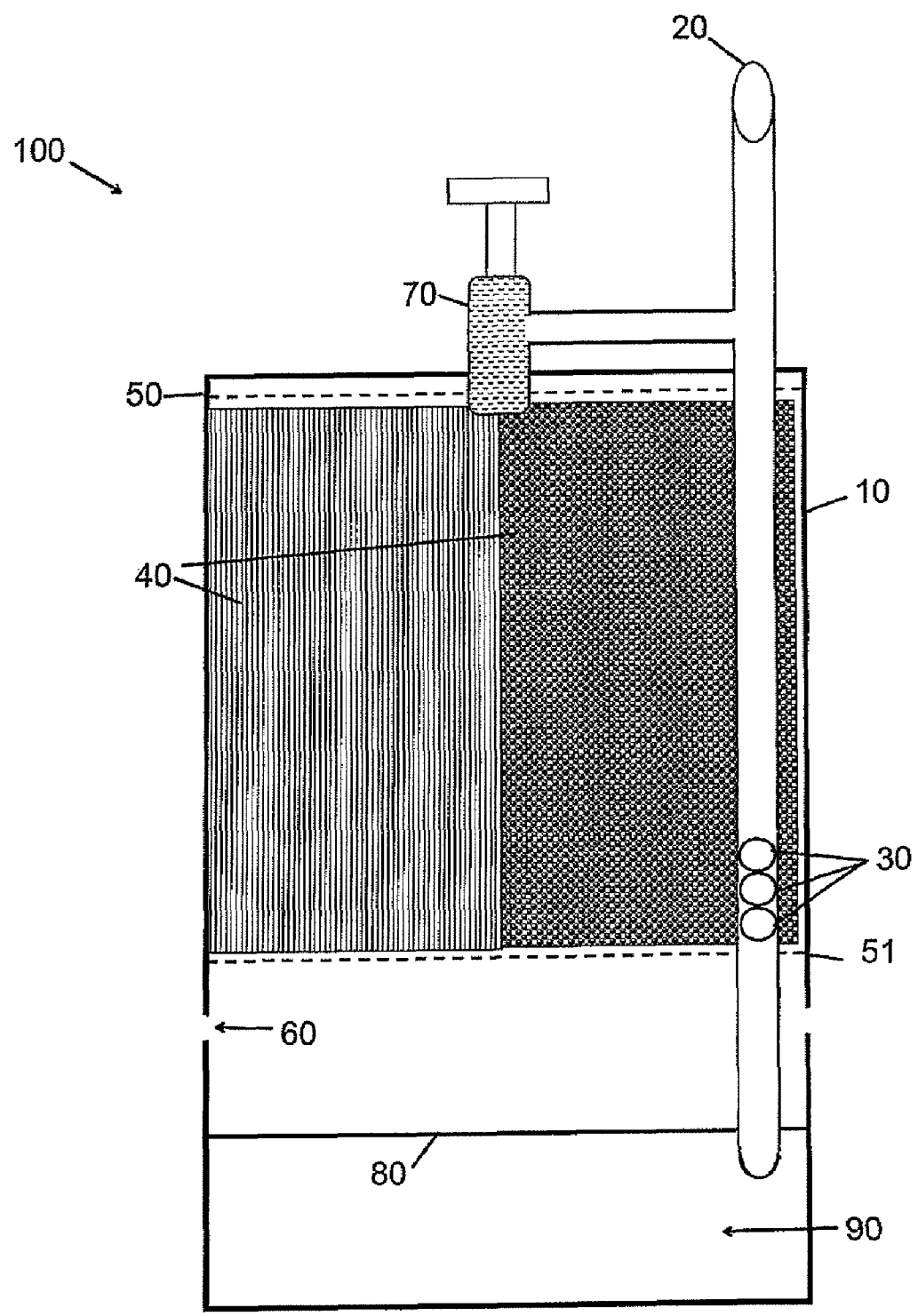

This application claims priority from U.S. Provisional Application No. 60/516,067 filed on Oct. 31, 2003.

BACKGROUND OF INVENTION

The present invention relates generally to an apparatus and method for growing and applying specific aerobic and facultatively anaerobic cultures of bacteria such as *Pseudomonas Fluorescens, Bacillus Subtilis, Bacillus Licheniformis, Bacillus Thuringiensis, Starkeya Novella* and sulfur metabolizing bacteria to soil bioremediation, biological pest management and wastewater treatment processes including carbonaceous BOD removal, grease digestion, denitrification, odor control, methane gas production, pond clarification and the restoration of the percolation rates in media such the soil that has clogged biomat. A principal application for this device is the biological reduction of nitrate contamination. The device has broad application where bacteria are used in industrial, agricultural, forestry and bioremediation processes.

There are many applications where bacteria may be used beneficially in residential, commercial, and industrial applications. Non-Pathogenic bacteria enhance either directly or indirectly through enzyme production many activities in all of society. In the area of wastewater treatment the benefits of creating an environment conducive to the growth and reproduction of beneficial bacteria has long been known. In other areas, such as the prevention of freezing and frost, it is being learned that bacteria can perform tasks heretofore expected of chemical agents. In nearly all cases the method has been to produce bacteria in an industrial setting and apply those bacteria on a continual basis or to adjust the environmental conditions and depend upon natural selection to have the correct species of bacteria grow on site.

A. Wastewater:

Wastewater contains pathogenic bacteria, carbonaceous compounds, nitrogenous compounds, odorous sulfur compounds, and grease. All of these pollutants have been traditionally stabilized with biological treatment processes. Many species of native bacteria accomplish the stabilization process in conventional secondary wastewater treatment. Biological nitrogen removal is an important aspect of wastewater treatment. Findings confirm the existence of a diverse community of heterotrophic bacteria in addition to *nitrosomonas, nitrobacter*, and *nitrosococcus*, which are involved in nitrogen removal during wastewater treatment. Of these heterotrophic bacteria, *Pseudomonas* spp. are known to be dominant denitrifiers and show significant involvement in both nitrification and denitrification processes. *Pseudomonas* bacteria have demonstrated direct oxidation of ammonium to nitrates with little or no nitrite accumulation. Both *Pseudomonas* and *Bacillus* spp. show significant involvement in nitrification. Soil bacteria such as *Pseudomonas Fluorescens, Bacillus Subtilis* and *Bacillus Licheniformis* to name three, are superior degraders of both carbon and nitrogen compounds. These soil bacteria are present in wastewater treatment processes in diminutive numbers along with many other species. Many of the other species originate from the human gut and are not aggressive degraders of carbon. These include coliform group bacteria. The soil bacteria that are cultured by the method and device described, do not naturally predominate in wastewater treatment processes as they do in soil. The device and methods are used to establish these bacteria as dominant cultures in such wastewater treatment processes.

In aerobic conditions the heterotrophic nitrifying bacteria *pseudomonas Fluorescens* can use an enzyme called ammonia monooxygenase (AmoA) to oxidize ammonia to hydroxylamine, nitrite, and nitrate with a small but significant release of nitrite and nitrate. The ammonia monooxygenase found in pseudomonas is thus similar to the amoA gene found in autotrophic ammonia oxidizers such as *nitrosomonas europaea*. The nitrate is reduced to nitrite and further reduced to nitric oxide (NO) under anaerobic conditions. Ref. (Daum M, Zimmer W, Papen H, Kloos K, Nawrath K, Bothe H. "Physiological and molecular biological characterization of ammonia oxidation of the heterotrophic nitrifier *Pseudomonas putida*." Curr Microbiol 1998 October; 37(4):281-8. Medline) Protein and other nitrogenous compounds are likewise broken down by respective enzymes. The stepwise pathway involved is as follows. In aerobic conditions Pseudomonas converts ammonia into nitrite and nitrate which is then reduced as the effluent flows into the anaerobic zone, and begins to act as an electron acceptor and oxidize carbon while being reduced by the denitrification pathway from Nitrate>Nitrite>Nitric oxide>Nitrous oxide>Nitrogen gas with the consumption of carbon into carbon dioxide or cell matter. In this process some of the carbon for denitrification is obtained through metabolic consumption of what is called the zoogleal biomat, an anaerobic assemblage of bacteria and other organisms that form a humic filter.

Approximately 25% of the US population relies upon decentralized wastewater treatment. This number is growing. Many systems are old and were not constructed in a way that offers the maximum protection of ground water. In these systems it is common for nitrogen to escape the treatment zone and enter the ground water.

The design of standard septic treatment and disposal systems relies upon anaerobic conditions in the septic tank and throughout the leach trench up to and inclusive of the biomat. Anaerobic conditions exist until the effluent passes through the biomat and hopefully enters into an aerobic treatment zone. In a standard anaerobic septic treatment system ammonia and reduced forms of nitrogen pass completely through the system almost unaltered. They are converted to oxides of nitrogen like nitrite, and nitrate after escaping the biomat and leaving the treatment zone. Under this form of treatment nitrate may enter the ground water and contaminate drinking water supplies. Nitrate in drinking water poses a health threat.

A further concern in onsite waste treatment is the fact that biomat growth tends to clog soil and creeping failure occurs as the soil percolation rate diminishes and effluent rises in the trench. This causes one common type of leach field failure, the surfacing of effluent. Unable to percolate and in excess of transpiration demand, the effluent will pool on the surface, following the occluded side walls of the trench. Such pooling brings humans and animals into contact with pathogens. This anaerobic biomat is sensitive to air and to the attack by aerobic bacteria and invertebrates such as nematodes. Aerobic bacteria are normally not present or long lived in the biomat. They are excluded except at the outside interface where predation by worms, nematodes, bacteria, and fungi occurs. Pseudomonas bacteria stimulate the predation of biomat by these invertebrate organisms and participate in the competitive inhibition on several levels. They encourage the invertebrate grazers and produce antibiotic compounds that competitively inhibit certain other bacteria such as the slime producing coliform.

The wastewater treatment described in U.S. Pat. No. 4,279, 753 entitled "Wastewater Treatment System Including Multiple Stages of Alternate Aerobic-Anaerobic Bioreactors in Series" to Nielson et al., is confined to improving and enhancing a natural biological process that removes suspended, dissolved organic matter and nitrogen from the wastewater. This is accomplished by a series of alternating aerobic-anaerobic bioreactors with the effluent stream contacting microorganism located within the bioreactors.

The process described in U.S. Pat. No. 4,042,458 entitled "Process For The Production Of Micro-organisms" to Harrison is specifically designed to improve the anaerobic digestion process by increasing the number of *Methylococcus* bacteria. This process involves placing pure strains of Pseudomonas into the process and does not involve growing the bacteria at the site of use.

The process described in U.S. Pat. No. 4,999,111 entitled "Process For Treating Water" to Williamson details a modification to the activated sludge process of treating wastewater. This modification is specifically designed to improve the removal of Phosphorus from the wastewater through the adjustment of environmental factors.

The method described in U.S. Pat. No. 6,383,390 entitled "Method Of Treating Ammonia-comprising Wastewater" to VanLoosdrecht, et al. reveals a two stage process for treating ammonia in a waste stream. The environmental conditions of the stages are adjusted and no microorganisms are added to either stage.

The process described in U.S. Pat. No. 6,447,681 entitled "Aquaculture Wastewater Treatment System And Method Of Making Same" to Carlberg, et al. is a three phase system specifically for treating waste from fish culture. The system utilizes macroorganisms, a traditional ammonia removal system, and constructed wetlands for treatment before dispersal. The system does not introduce any outside microorganisms.

The system described in U.S. Pat. No. 6,497,819 entitled "Method and Apparatus For Treating Wastewater" to Baba, et al. discloses a device to be put into direct contact with the wastestream for the treatment of that wastestream. It utilizes a macromolecular substance to house the microorganisms which provide treatment. The system does not utilize any selection or inoculation.

B. Petroleum Hydrocarbon Contamination of Soil and Water:

Petroleum hydrocarbon originating from refineries, crude oil drilling operations, pipeline breaks, leaking underground storage tanks, and spills on land and sea, are a major source of pollution. The bacterial formulation described in U.S. Pat. No. 5,531,898 entitled "Sewage And Contamination Remediation And Materials For Effecting Same" to Wickham discloses use of bacteria including: *Pseudomonas Fluorescens, Bacillus subtilis,* and *Bacillus licheniformis*. These are, in the case of pseudomonas, aerobic and, in the case of bacillus, facultative anaerobic heterotrophic bacteria. These bacteria have been shown to digest crude oil, diesel, BTEX, and most forms of TPH. They have applications in the bioremediation of soil and aquatic petroleum contamination as a biodegrader, a source of enzymes for cleaving hydrocarbons. Rapid or accelerated bioremediation of major petroleum contamination sites, requires enormous numbers of these bacteria. A method for such quantities was not readily available, and this resulted in increased cost to end users. In order to produce large numbers of these bacteria rapidly it was necessary to develop an aerobic bacteria generator such as the device and method described in this patent.

The microorganism and method described in U.S. Pat. No. 6,521,444 entitled "Microorganism And Method For Environmental Purification Using The Same" to Numata, et al. is a novel microorganism which has been altered to allow it to be efficient at decomposing trichlorethlyne. It is a very specific microorganism which serves a very specific purpose.

The process described in U.S. Pat. No. 6,569,333 entitled "Restoring Soil And Preventing Contamination Of Groundwater" to Takagi, et al. describes a method to selectively grow bacteria on agar. The bacteria are then mixed with a porous media which is then mixed with the soil to be treated. The porous material traps contaminants and water flow until treatment is completed.

The method described in U.S. Pat. No. 6,368,019 entitled "Method for soil remediation" to Sugawa, et al. reveals a process to inject liquid containing a specific group of microorganisms into the earth near a site contaminated with hydrocarbons. The injection of the liquid forces volatile components out of the soil pores and they are captured at the surface. The microorganisms effect treatment of the small amount of remaining contaminant. The microorganisms are not grown at the site, but manufactured in an industrial setting.

C. *Phytophora, Pythium* Damping Off, Bacterial, Viral, and Fungal Plant Diseases

*Phytophora infestans* was the cause of late blight of potatoes and was responsible for the Irish potato famine of 1845. The organism grows on leaves. The disease, which can destroy a field crop within days, causes mottled, dark lesions on leaves and stems from which develop a white, velvety growth that kills the plant. Blighted potatoes develop a dark, corky rot and appear dehydrated. It is a virulent and contagious disease. Hyphae grow between the cells thrusting haustoria into neighboring cells and also grow through stomates of leaves which then develop into branched sporangiophores. Raindrops help spread sporangia to other plants. One variety is now responsible for a recent outbreak of sudden oak death in the United States caused by *Phytophthora ramorum*. This disease attacks oak, bay, Douglas fir, redwood, rhododendron, madrone, grape, and many other valuable fruit, timber and ornamental species.

*Pseudomonas fluorescens* and *Pseudomonas corrugata* have been tested as biocontrol agents against *Pythium* damping off of sugar beet. Incorporation into the seed coat offers a practical way of applying the biocontrol agents. For optimization of biocontrol, the determination of the minimum initial dose necessary for successful biocontrol is crucial. (Schmidt, C. S.; Agostini, F.; Mullins, C. m.; Leifert, C., Influence of Initial Antagonist Dose on Sugarbeet Root Colonization and Biocontrol of Pythium Damping Off, University of Aberdeen, Department of Plant and Soil Science, and Aberdeen University Centre for Organic Agriculture (AUCOA), Aberdeen UK)

Antagonistic performance of *Pseudomonas fluorescens* increases with dosage. Doses larger than 107 CFU/seed pellet are necessary to inhibit *Pythium* damping off disease. Conversely, antagonistic performance of *Pseudomonas corrugata* follows an optimum curve. Numbers of healthy plants as well as plant fresh and dry weight reach highest levels when 104-106 CFU/seed pellet are applied and these indicators decrease at higher doses. The ratio between applied bacteria (CFU/seed pellet) and recovered bacteria per plant clearly shows that the applied Pseudomonas strains not only persist but also propagate on the seedling surfaces. Both Pseudomonas strains are able to build up large populations ($1-3\times10^5$) on sugarbeet seedlings even when low initial doses (103 CFU/seed pellet) are applied. At low doses, up to 80-300 fold more cells than initially applied can be recovered. At doses exceeding 105-106 CFU/seed, however, the total population per seedling of the *Pythium* damping off antagonist does not increase, and, in fact, the number of cells recovered decreases compared to initial dose. Thus, a saturation point appears to be reached with 105-106 CFU/plant. Population sizes of both antagonists reach maximum levels (>104 CFU/cm) at the hypocotyl and the upper parts of the root (0-2 cm below seed level) already when the lowest dose is applied (103 CFU/seed pellet). Measurable bioluminescence indicates high metabolic activity of the strains in the hypocotyl and the upper parts of the root at all applied doses. In Pseudomonas corrugata, population size does not increase with dose at all whereas in *Pseudomonas fluorescens* a slight, but significant increase of the total population per plant with dose is observed, due to an increased colonization of the lower root parts (exceeding 4 cm root depth). Not only the population size but also differences in the velocity of the population build up and in antibiotic production at different initial doses may account for the observed significant effects of dose on biocontrol efficacy. Downward colonization of sugarbeet roots by Pseudomonas fluorescens is significantly increased in five different soils by combining it with *Bacillus subtilis* in a mixed inoculum. (Schmidt, C. S.; Agostini, F.; Whyte, J.; Simon, A. M.; Mullins, C. M.; Leifert. C., Influence of Soil pH. Soil Temperature and Soil Type on Biocontrol of Pythium Damping Off Disease by Antagonistic Bacteria, University of Aberdeen, Department of Plant and Soil Science, and Aberdeen University Centre for Organic Agriculture, Aberdeen UK).

The material and method revealed in U.S. Pat. No. 4,952,229 entitled "Plant Supplement And Method For Increasing Plant Productivity And Quality" to Muir details a soil supplement to be manufactured. The supplement consists of a specific mix of microorganisms which are designed to improve plant growth. The supplement is applied in the solid form.

The process described in U.S. Pat. No. 5,507,133 entitled "Inoculant Method And Apparatus" to Singleton, et al. is designed for the specific purpose of growing rhizobia to inoculate legumes. The system utilizes prepackaged units with two compartments: one containing peat moss as a substrate and the other containing pure cultures of *rhizobia*. The units are shipped to the site of inoculation, mixed, and inoculation takes place after a growth period.

The device described in U.S. Pat. No. 6,432,698 entitled "Disposable Bioreactor For Cultivating Microorganism And Cells" to Gaugler, et al. describes a system for the production of a specific nematode organism to be used as a biological pesticide. The system is designed to be shipped to a site and the product utilized after an incubation period. The system utilizes no aqueous phase.

D. Hog, Dairy and Aquaculture.

*Bacillus subtilis* is used in aquaculture for applications such as the larval rearing of the white shrimp *Penaeus schmitti*. In this application there are two benefits. *Bacillus subtilis* is useful in controlling the gut epithelium scaling syndrome of *Penaeus schmitti*, known as "Bolitas." This has beneficial effects upon survival, metamorphosis rate, larval quality and size of the postlarval shrimp. The antibiotic activity permits a reduction in the daily water exchange rate from 100% to 30% in the larval rearing process.

The process described in U.S. Pat. No. 4,927,751 entitled "Process For Obtaining Exoenzymes By Culture" to Memmer, et al. reveals a two step process which uses a highly complex fermentation unit. This process is limited to the production of enzymes only.

The process described in U.S. Pat. No. 5,283,059 entitled "Process For The Producing A Stabilized Spore Forming Viable Microorganism Preparation Containing *Bacillus Cereus*" to Suzuki, et al. provides for the growth of specialized bacteria in a starch solution. This solid mixture is then pelletized and used as animal feed.

The method described in U.S. Pat. No. 5,967,087 entitled "Method Of Increasing Seafood Production In The Barren Ocean" to Markels, Jr. relates to the addition of fertilizer to ocean areas. This addition of fertilizers and iron chelates increases seafood production by stimulating aquatic plant growth. No microorganisms are grown utilizing this system.

The process described in U.S. Pat. No. 6,183,739 entitled "Phospholipase In Animal Feed" to Baudeker, et al. involves a method to increase feed utilization in animals by adding phospholipase to the animal feed.

In each of the cases cited above the system described either modifies the environment, provides an additive, or adds microorganisms to a process. In no case is there a system which provides for the continual growth of specific microorganisms at a site where they are needed. The systems depend upon a laboratory to provide large quantities of microorganisms which are at a much higher purity than needed for many uses.

There remains a need for a simple device that can be inoculated with bacteria and will grow bacteria for inoculation into an in situ process or treatment. Further, the need exists for a method to provide these bacteria in quantity over long periods of time. There is a further need for microorganisms to be produced in an aqueous solution to allow for ease of handling.

SUMMARY OF THE INVENTION

It is an aspect of the invention to provide a simple, cost-effective, and space-saving device to provide specific bacteria in applications where they are beneficial.

It is another aspect of the invention to provide a system that produces large populations of specific bacteria to wastewater treatment systems which need said bacteria for improved operation.

It is yet another aspect of the invention to provide specific bacteria in aqueous phase to commercial applications for industrial or agronomic benefit.

It is a further aspect of the invention to provide specific bacteria at a location that has a significant effect at a location distant to the point of application.

These and other aspects of the invention are obtained by providing a growth area for specific bacteria which are inoculated into the growth area where the bacteria are allowed to grow and reproduce and be exported from the unit. The apparatus for the growth of the specific bacteria comprises a housing, which has one or more porous sides and which is placed in an aqueous environment, a medium in the housing for the attachment of the specific bacteria while growing, and an injection point for gas to provide mixing of the desired bacteria and liquid from the aqueous environment. Within the housing there is a receptacle into which the bacteria inoculant is placed. A gas mixture that supports the growth of the desired bacteria is injected into both the housing and the receptacle separately, with the injection point being near the bottom of the housing and the receptacle to facilitate mixing of the bacteria, the gas and the liquid. The turbulence created by the rising gas causes sloughing of bacterial cells within the housing, thereby allowing bacteria to exit the housing as liquid from the aqueous environment exits the housing. The rising of the gas mixture within the housing causes an upward flow of the liquid within the housing.

BRIEF DESCRIPTION OF THE DRAWINGS

The present invention will be more fully understood and appreciated by reading the following Detailed Description in conjunction with the accompanying drawing, in which:

FIG. 1 is a side sectional view of the preferred embodiment of the invention.

DETAILED DESCRIPTION OF THE INVENTION

FIG. 1 shows an apparatus 100 to accomplish the process of the growth and culturing of microorganisms. The apparatus 100 comprises an outer housing 10, a gas inlet line 20, a gas injection means 30, a microbial growth medium 40, growth medium retention means 50 & 51, a liquid inlet 60, and a microbial inoculant receptacle 70.

The apparatus 100 is placed in an aqueous material that will support the growth of the desired microorganisms. In the static condition all parts of the apparatus 100 are in fluid communication with all other parts of the apparatus 100. The outer housing 10 is constructed of any material such as plastic, metal, or concrete which will not deteriorate when in contact with the aqueous material into which it is placed. The outer housing 10 may be any shape or size in horizontal cross section and may be any height as determined by the depth of the aqueous material or other factors.

Preferably, the housing 10 is columnar, having a height of approximately 3 feet and a diameter of approximately 18 inches. The principles of the present invention, however, are not dependent on a specific size or shape for the housing, so a wide variety of sizes and shapes is acceptable. Generally, the size of the housing 10 will increase with the size of the vessel in which it is to be placed. Preferably, the housing 10 must be of such a size that it can be submerged in the aqueous material. The housing 10 is open at its top surface and bottom surface to allow flow of liquid into and out of the housing 10.

The gas inlet line 20 is constructed of any commonly available piping material such as steel, copper, rubber or plastic. The gas inlet line is in fluid communication with a source of gas under positive pressure sufficient to cause gas flow into and through the gas inlet line 20 towards gas injection means 30. The gas inlet line 20 must be large enough to provide sufficient gas to the housing to feed the microorganisms being cultured in the housing 10 and to create an upward flow of gas, as described hereinbelow. Preferably, the gas inlet line is approximately ½ inch in diameter.

The gas injection means 30 is a porous material that will allow fluids to pass through the pores in the material. The material of gas injection means 30 may be any material with the ability of passing a gas through itself such as rubber, stone, plastic, or steel. The size of the pores of the gas injection means 30 is dependent upon the needs of the microorganisms under culture and the gas being passed through said gas injection means 30. Preferably, the gas injection means 30 is a ring-shaped metal tube that has been perforated to allow gas to pass.

The gas injection means 30 is placed within the housing 10 so as to effect an upward flow of the aqueous material when gas is released from the gas injection means 30.

The microbial growth media 40 is a porous material capable of growing bacteria on the surface of the media. It may be of any material which provides support to bacterial colonies, including plastic, wood, stones, sand, or metal. The pores of the microbial growth media 40 should be of sufficient size, shape, and configuration so as to not inhibit to any great degree the fluid movement through the microbial growth media 40. The microbial growth media 40 should have the characteristic of being able to slough the microbial growth at such an interval and in such a way so as to not prevent the fluid movement through the microbial growth media 40.

The growth media retention device 50 & 51 is placed on all sides of the microbial growth media 40 as needed to assure that the microbial growth media 40 stays within the housing 10 and does not exit the housing 10 with the flow of liquid through the housing 10. The growth media retention device 50 & 51 may be of any material that allows free flow of liquid and will not pass the microbial growth media 40 such as plastic, textile, wood, or steel. The pores of the media retention device 50 & 51 are sufficiently large to allow free passage of liquid and sufficiently small to prevent the movement of the growth media 40 from passing.

The liquid inlet holes 60 are of a size, shape, number, and nature so as to allow free flow of liquid into the housing 10. Optionally, an extension may be placed upon said holes to place the apparatus in fluid communication with an area remote from the immediate base of the unit.

The microbial inoculant receptacle 70 is a chamber capable of holding a mixture of microorganisms initially in a dormant state which are activated upon being hydrated. The microbial inoculant receptacle 70 is porous and constructed to limit the amount of fluid flow into and out of the receptacle. The receptacle is in communication with a branch of the gas inlet line 20 which supplies gas to the area of the microorganisms in said housing. Preferably the branch of the gas inlet line 20 that provides gas to the microbial inoculant receptacle 70 is ⅛ to ¼ inch in diameter and contains a diffuser at the point that it enters the microbial inoculant receptacle 70. The flow of gas into the microbial inoculant receptacle 70 is sufficient to provide transfer by diffusion of the gas into the liquid within the microbial inoculant receptacle 70 and not sufficient to cause turbulence within the receptacle. Optionally, the rate of flow of gas into the microbial inoculant receptacle 70 can be controlled by a valve, orifice, or other similar device. The microbial inoculant receptacle 70 preferably is accessible from the outside of the housing 10 so that additional microbial inoculant can be added depending on the microorganisms being cultured. Generally, the microbial inoculant receptacle 70 will be made of plastic material.

During operation a gas mixture is delivered through the gas inlet line 20 to the gas injection means 30. The gas mixture is forced through the porous area of the gas injection means 30 and into the fluid within the apparatus. The pores of the gas injection means 30 are selected to assure the appropriate combination of turbulence and gas transfer rate into solution based upon the needs of the microorganisms to be grown and the gas being utilized. Upon entering and mixing with the fluid within the apparatus 100 a portion of the gas dissolves into the fluid and a portion of the gas causes an upward flow of the fluid within the apparatus 100. The upward flow creates a low pressure area at the base of the unit which causes flow from around the apparatus 100 through the liquid inlet holes 60.

The type of gas supplied to the apparatus 100 will depend on the microorganisms to be cultured. In many cases, atmospheric air will be used. In other cases, digester gases such as hydrogen, oxygen, methane, carbon monoxide, carbon dioxide, nitrous oxide, nitric oxide, or a combination thereof, will be used.

The gases dissolved in the liquid within apparatus 100 are carried into close proximity of microorganisms within the fluid mixture, microorganisms within the microbial inoculant receptacle 70, and microorganisms attached to the microbial growth media 40. The gases support the growth and reproduction of these microorganisms. The liquid exits the housing 10 from the top of the housing 10 moving upward and outward from the apparatus 100. The turbulence caused by the flow of the fluid upward through the microbial growth media 40 causes the microorganisms within the unit to slough and to join the flow of liquid within the housing 10. These microorganisms are carried away from the housing 10 within the fluid flow.

The liquid of the aqueous environment is contained within a vessel (not shown). Vessel, as used herein, means any closed or open means of containing liquid, such as a tank, a pond, a lagoon or other similar structures. When the apparatus 100 is used to produce bacteria for the treatment of wastewater, the vessel can be, for example, a septic tank or sewage lagoon. When the apparatus 100 is used to produce bacteria for application to a road, crop field or land contaminated by hydrocarbons, the vessel can be, for example, a closed tank that can be transported to the site where the beneficial bacteria are to be applied.

The method described herein can be divided into four overlapping phases of operation. Phase one is the Gas Injection Phase, Phase two is the Bacterial Inoculation and Growth Phase, Phase Three is the Sloughing Phase and Phase four is the Application Phase.

Phase one of the process involves the injection of gas into the interior of a housing and the incorporation of that gas into solution in an aqueous solution. The injection of gas causes several important effects within the housing and the surrounding aqueous material. The gas which is in solution will provide a hydrogen acceptor in biochemical reactions and/or one or more essential nutrients for the growth of specific bacterial cultures to be grown within the housing. Excess amounts of said gas which do not go into solution will provide upward movement due to their buoyancy and cause an up flow through all parts of the housing in a method often referred to as an air lift action.

Phase two of the process involves the growth of bacterial colonies on a media conducive to said growth. The specific species of bacteria will be dependent upon the species introduced initially into the system as well as the environmental growth factors within the system. Said bacterial growth shall be at a rate so as to provide a constant supply of bacteria for additional phases as well as to maintain a population of bacteria within the bacterial growth media of the unit.

Phase three of the process is the sloughing of the bacterial growth off of the growth media and into suspension within the aqueous material. Said sloughing takes place due to the combined scouring effect of the injected gas which is not in solution, the upward flow of the aqueous material, and movement of the bacterial growth media. The sloughing action is performed to such a degree so as to allow continuation of colonies for phase two to continue as well as providing sufficient amounts of bacteria to accomplish tasks as indicated in phase four.

Phase four of the method involves the removal of bacteria within the aqueous material to an area which requires the continued action of bacterial populations to effect a desired outcome. Examples of such applications would include, but not be limited to, biologically mediated oxidation and reduction reactions, the conversion of hydrocarbons into elemental end products, the dissolution of the biomat in soil based wastewater treatment system, the prevention of disease in flora, or the prevention of disease in animals. Said application generally involves the movement of the aqueous solution to the location of needed bacteria.

More specifically, the method of growing beneficial bacteria according to the present invention begins with providing a vessel that contains liquid that can be used to support growth of beneficial bacteria. Vessel, as used herein, means any closed or open means of containing liquid, such as a tank, a pond, a lagoon or other similar structures. The treatment assembly, as disclosed above, which contains a bacterial growth medium, is then inserted into the vessel. Next, inoculant microorganisms are selected, based on the desired beneficial microorganisms, which in turn are based on the objective of the desired application.

The inoculant microorganism is placed in the treatment assembly's microbial inoculant receptacle from whence the liquid carries it to the growth medium. In the presence of liquid that supports its growth, the inoculant microorganism multiplies on the growth medium. Gas is injected into the treatment assembly to cause an upward flow of liquid in the assembly. As gas and liquid flow through the treatment assembly, the flow assists in sloughing the beneficial microorganism from the growth media and carries the microorganisms out of the assembly.

It is commonly accepted that municipal wastewater treatment systems modify environmental conditions such as temperature, pressure, pH, alkalinity, salinity, substrate material, nutrients, and/or electron acceptors to optimize the bacterial populations present. Such daily adjustment as changing external heating, increasing dissolved oxygen content, adding an alkalinity source, or adding nutrients are common place. Systems are designed to consider such factors as insulation of treatment units, enclosure to allow for pressure increases, and alternative feed sources. The purpose of these environmental modifications is to assure that bacterial growth and reproduction are maximized in relation to the treatment process. In a similar way the growth of any one pure strain, or combination of several pure strains can be optimized by adjusting the environmental conditions within a system.

Means can be provided to control environmental conditions in the treatment assembly. For example, the temperature of the treatment assembly can be controlled by raising or lowering the temperature of the gas and/or liquid introduced into the treatment assembly. Similarly, the salinity and/or alkalinity of the liquid can be controlled by the addition of compounds that raise or lower salinity and/or alkalinity. Providing an appropriate gas is also important, for example, in producing beneficial microorganisms that are anaerobic. While gas must be introduced in the treatment assembly to provide upward flow of liquid, gases other than oxygen can be introduced when the desired beneficial microorganism is anaerobic.

In some cases it may be necessary to introduce additional inoculant microorganisms. Additional inoculant microorganisms can be additional quantities of a previously introduced strain of inoculant microorganism or they can be a different strain of inoculant microorganism intended to produce a different beneficial microorganism.

The application for which the beneficial microorganisms will be used determines which microorganism will be generated and how it will be harvested and/or applied. For certain purposes, for example when the beneficial organisms will be used to treat conditions within the vessel, it is sufficient to allow the beneficial microorganisms to flow out of the treatment assembly and into the liquid in the vessel. For other purposes, for example when the beneficial microorganisms will be sprayed on crops to prevent Pythium damping off, the beneficial microorganisms must be harvested from the vessel. Harvesting can be accomplished by removing a portion of the liquid from the vessel, which portion will have an increased population of the beneficial microorganism. To maintain production of beneficial microorganisms, additional liquid must be added to the vessel as beneficial microorganisms are harvested.

For certain purposes, the effective agent is an enzyme produced by the beneficial microorganism. For some of the purposes described elsewhere in this application, beneficial organisms produce one or more of the following enzymes, which are effective to treat the problem presented: amylase (1,4-alpha-D-Glucan-glucanhydrolase), lipase, protease, amylase, lipase, ammonia monooxygenase, Nitrous Oxide Reductase, RagCthus, Nitrite Reductase, Nitrate Reductase, and Nitric Oxide Reductase. For example, the effective agent in the initial steps of denitrification of wastewater is ammonia monooxygenase, which is produced by the pseudomonas Fluorescens microorganism. As is known in the art, it is possible to genetically modify microorganisms to produce specific enzymes. Such genetically modified microorganisms are included in the beneficial microorganisms that are part of the present invention.

While there has been illustrated and described what is at present considered to be the preferred embodiment of the invention, it should be appreciated that numerous changes and modifications are likely to occur to those skilled in the art. It is intended in the appended claims to cover all those changes and modifications that fall within the spirit and the scope of the present invention.

We claim the following:

1. A method of treating a liquid in a vessel, comprising the steps of:
   a. submerging an enclosed treatment assembly into said vessel, wherein said treatment assembly comprises:
      (i) a housing defining a chamber therein and including at least one opening in the bottom of said chamber and at least one opening in the top of said chamber to allow said liquid to flow into and out of said chamber;
      (ii) a gas inlet in fluid communication with the bottom of said chamber of said housing; and
      (iii) a microbial growth medium supporting microorganisms positioned in said housing;
   b. injecting gas through said gas inlet into said chamber of said housing; and
   c. dispersing said gas in said chamber of said housing such that said gas mixes with said liquid in said chamber and causes said liquid to flow upwardly though said chamber and over said microbial growth medium.

2. The method of claim 1 further comprising the step of harvesting said microorganisms.

3. The method of claim 1 wherein the liquid is wastewater.

4. The method of claim 1 wherein the liquid is a nutrient broth that comprises elements from the group consisting of carbon, nitrogen, phosphorous, iron, magnesium, sulfur, sodium, potassium, chlorine, calcium, combinations thereof and salts thereof.

5. The method of claim 1 wherein said microorganisms are selected from the group consisting of *Pseudomonas fluorescens, Bacillus subtilis, Bacillus licheniformis, Bacillus thuringiensis, Starkeya novella* and combinations thereof.

6. The method of claim 1 wherein said microorganisms comprise microorganisms that produce enzymes from the group consisting of amylase (1,4-alpha-D-Glucan-glucanhydrolase), lipase, protease, amylase, lipase, ammonia monooxygenase, Nitrous Oxide reductase, RagCthus, Nitrite reductase, Nitrate reductase, and Nitric Oxide reductase.

7. The method of claim 6 further comprising the step of genetically modifying a microorganism to cause it to produce the selected enzyme.

8. The method of claim 1 wherein the step of injecting a gas comprises introducing gas bubbles to form a biofilm at the gas-liquid interface.

9. The method of claim 1 comprising the additional step of manipulating environmental conditions to promote growth of said microorganisms.

10. The method of claim 9 wherein the manipulated environmental conditions are selected from the group consisting of temperature, pressure, alkalinity, and salinity.

11. The method of claim 1 wherein said microorganism is aerobic bacteria.

12. The method of claim 1 wherein the step of injecting gas comprises controlling the volume of gas.

13. The method of claim 1 wherein said microorganism is selected from the group consisting of anaerobic bacteria, facultative bacteria, fungal organisms and combinations thereof.

14. The method of claim 1 wherein said growth medium is selected from the group consisting of plastic, wood, naturally-occurring geomorphic material, fabric and metal.

15. The method of claim 1 wherein said growth medium is spherical in shape.

16. The method of claim 1 wherein said growth medium is columnar in shape.

17. The method of claim 1 wherein said growth medium is self cleaning through the scouring action of said step of injecting gas through said gas inlet into said housing.

18. The method of claim 1 comprising the additional step of regularly sloughing said microorganisms into said liquid.

19. The method of claim 1 wherein said growth medium is restrained within said treatment assembly by a grating.

20. The method of claim 1 wherein said growth medium is restrained within said treatment assembly by a net.

21. The method of claim 1 wherein the gas is selected from the group consisting of air, methane, carbon dioxide, hydrogen, anaerobic digester gas and combinations thereof.

22. The method of claim 1 comprising the additional step of diffusing said gas.

23. The method of claim 1 wherein said vessel is selected from the group consisting of septic tank, lagoon, a lake, a pond, a treatment tank, a grease trap and a portable tank.

24. The method of claim 1 comprising the additional step of removing said liquid from said vessel for use external to said vessel.

25. The method of claim 1 comprising the additional step of dispersing said microorganisms for use distant from said vessel.

26. The method of claim 25 wherein the step of dispersing said microorganisms comprises dispersing said beneficial organisms in a location where the benefits derived are selected from the group consisting of vector control of nuisances and pathogens, control of diseases or conditions on plant surfaces, augmentation of nutritional quality in animal rearing, and decontamination of soil that is contaminated by organic compounds.

* * * * *